United States Patent [19]
Shimodaira et al.

[11] Patent Number: 5,800,162
[45] Date of Patent: Sep. 1, 1998

[54] DENTAL-CARE DEVICE

[75] Inventors: Kenichi Shimodaira; Junichi Hayashi; Michio Ito, all of Nagano-ken, Japan

[73] Assignees: Injex Corporation; Matsumoto Dental College, both of Nagano, Japan

[21] Appl. No.: 758,451

[22] Filed: Nov. 29, 1996

[30] Foreign Application Priority Data

Dec. 1, 1995 [JP] Japan .................. 7-313865

[51] Int. Cl.$^6$ .................. A61C 3/00
[52] U.S. Cl. .................. 433/8; 433/9
[58] Field of Search .................. 433/8, 9, 173

[56] References Cited

U.S. PATENT DOCUMENTS

| | | | |
|---|---|---|---|
| 4,100,678 | 7/1978 | Yatabe | 433/9 |
| 5,503,558 | 4/1996 | Clokie | 433/173 |
| 5,573,401 | 11/1996 | Davidson et al. | 433/8 |
| 5,613,849 | 3/1997 | Tanaka et al. | 433/9 |

FOREIGN PATENT DOCUMENTS

A-6-14942  1/1994  Japan .

*Primary Examiner*—John J. Wilson
*Attorney, Agent, or Firm*—Oliff & Berridge, PLC

[57] ABSTRACT

A dental-care device is constructed from a planar base and a wire receiving part positioned on the top surface of the planar base. Slots extending straight horizontally are formed at the center of the wire receiving part, and wire is passed through these slots. The device is preferably manufactured by a metal powder injection molding method, and is composed of metal material which contains Ti as the base component, C in an amount of from about 0.03–0.5 wt % by weight of the metal material, O in an amount of from about 0.08–0.8 wt % by weight of the metal material, and N in an amount of from about 0.03–0.6 wt % by weight of the metal material. A large number of pores may be scattered at least in the vicinity of the surface of the metal material. This device can be easily manufactured, has a good surface wetness characteristic, and has functional portions, such as portions of low friction and portions of superior adhesiveness.

26 Claims, 8 Drawing Sheets

DENTAL-CARE DEVICE

BACKGROUND OF THE INVENTION

The present invention provides a dental-care device, such as braces for orthodontal correction, that is easy to manufacture, has good surface wetness, particularly with regard to saliva, and in which functional portions, such as portions of low friction and portions of superior adhesiveness, can be easily obtained.

DESCRIPTION OF RELATED ART

As a dental-care device used within the oral cavity, orthodontal braces and wire(s) for use in orthodontal correction of the teeth alignment (row of teeth) are known.

Braces for orthodontal use (referred to below simply as "orthodontal braces") generally comprise a base that is bond fixed to the teeth, and a wire receiving part formed on the top of the base. The wire receiving part has a slot through which wire is passed through. By tightening the wire, taut bridging of the teeth alignment is achieved.

For these kinds of braces, materials such as: 1) metal materials, i.e., stainless steel; 2) ceramics, i.e., those in the zirconia, alumina, and sapphire groups; and 3) hard plastics, i.e., polycarbonates and poly-dimethacrylates, have conventionally been used. However, the following types of defects can be found in any and all of these materials.

Braces made of stainless steel compare unfavorably in suitability for use in the body. In particular, there are deleterious effects on body tissue, causing allergies to metal, or concerns about carcinogens resulting from the elution of Ni and Cr. The appearance of the braces worn by the user is also inferior due to metal luster. Moreover, there is low wetness on the surface with regard to saliva, with the result that dryness easily occurs during use. Further, the lubricating ability of stainless steel compares unfavorably with body tissues such as the mucous membranes of the lips or skin. Accordingly, inflammation may result, causing pain to the patient.

Braces made of ceramic are of a low intrinsic toughness. Therefore, breakage easily occurs during wearing and use of the braces. In particular, it is necessary to exercise care when removing the braces after completion of orthodontic correction of the teeth to prevent breakage. Furthermore, braces made of ceramic are extremely expensive.

Braces made of hard plastic are of low strength and resistance to friction, so that deformation and breakage easily occur. Further, it is difficult to effectively transmit the stress from the tensed wires to is the teeth. Moreover, in the same way as in the stainless steel manufacture, there is poor wetness on the surface with regard to saliva, therefore the same problems occur. Furthermore, there is a great deal of sliding resistance from the wires against the inner surface of the slot, making it difficult to correctly perform minute load adjustments. Moreover, abrasion easily occurs during use.

In recent years, new materials such as Ti or Ti alloys have been proposed for use in orthodontal braces (JP Laid Open Patent 6-14942). Ti or Ti alloys are superior in that they are of light weight and high strength, anticorrosive and compatible with body tissue. However, manufacture and processing of the braces is not easy because it requires cutting machining, using special tools, or laser machining of the cast. The cast can also be formed by super-plastic formation processing. In particular, in processing the material into its complicated and minute form, a complicated manufacturing process and a high degree of skill are necessary, increasing manufacturing costs.

Moreover, particularly in the case of cast articles, the metal structure is very dense. Therefore, there is low surface wetness with regard to saliva, and, as a result, the same problems occur. There is also a comparatively greater sliding resistance of the wires against the inner surface of the slots, causing difficulty in properly making minute load adjustments.

A further problem is the reaction of oxygen or nitrogen during casting, causing the braces to be brittle. This creates the same problems as in ceramic braces.

SUMMARY OF THE INVENTION

The dental-care device of the present invention is lightweight and has sufficient mechanical strength and hardness in addition to the appropriate ductility and elasticity. The dental-care device also has parts which are superior to conventional braces of stainless steel, ceramic or plastic in adhesiveness, sliding characteristics of the wire and the like, anti-friction, and surface wetness characteristics. Furthermore, the dental-care device is superior in compatibility to body tissue, appearance, and ease of removal.

In particular, in a case having a surface layer, the sliding characteristic of the wire and the like, and anti-friction, is even more improved. In a case having pores in the vicinity of the surface, adhesiveness, surface wetness, and appearance are even more improved.

In a case where the manufacturing is performed by a metal powder injection molding method, even a complicated and minute formation can be easily manufactured with a high degree of accuracy and good reproducibility.

DETAILED DESCRIPTION OF PREFERRED EMBODIMENTS

The dental-care device of the present invention is explained below in detail based on the preferred embodiments shown in the attached figures.

As shown in the figures, the orthodontal corrective braces 1 are composed of a planar base 2, comprising a braces base and a brace(s) stem, and a wire receiving part (tie-wing) 3 formed on the top surface of the base 2.

Figure 3:
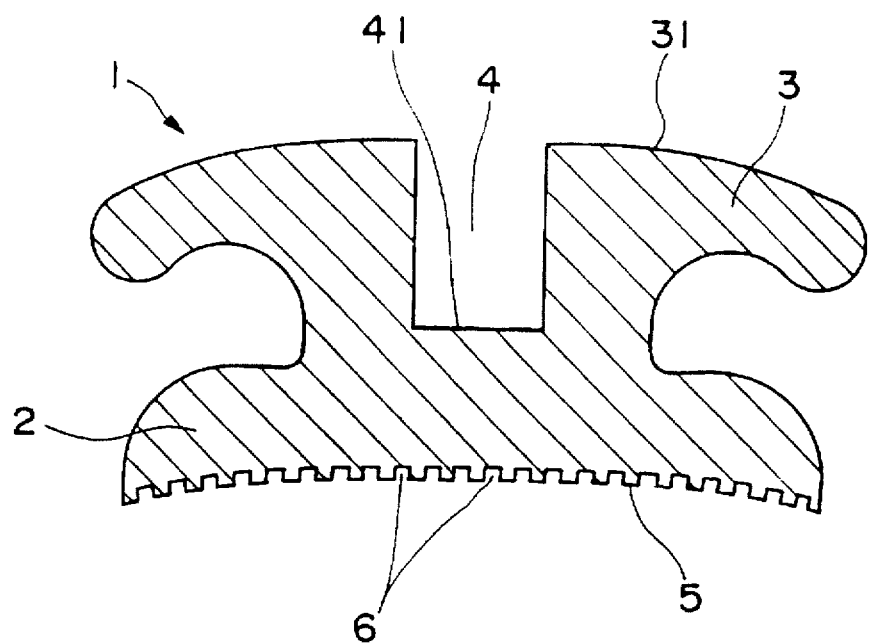
FIG. 3 is a cross-sectional view taken along line III—III of FIG. 1.

Slot 4 is formed extending straight at the center of the wire receiving part 3, through which wire 7 passes. The details of the wire will be described below. As shown in FIG. 3, the cross-section of slot 4 in the preferred embodiment has a rectangular shape; however, the embodiment is not limited to this; for example, it may be a V-shaped or a U-shaped slot.

Figure 4:
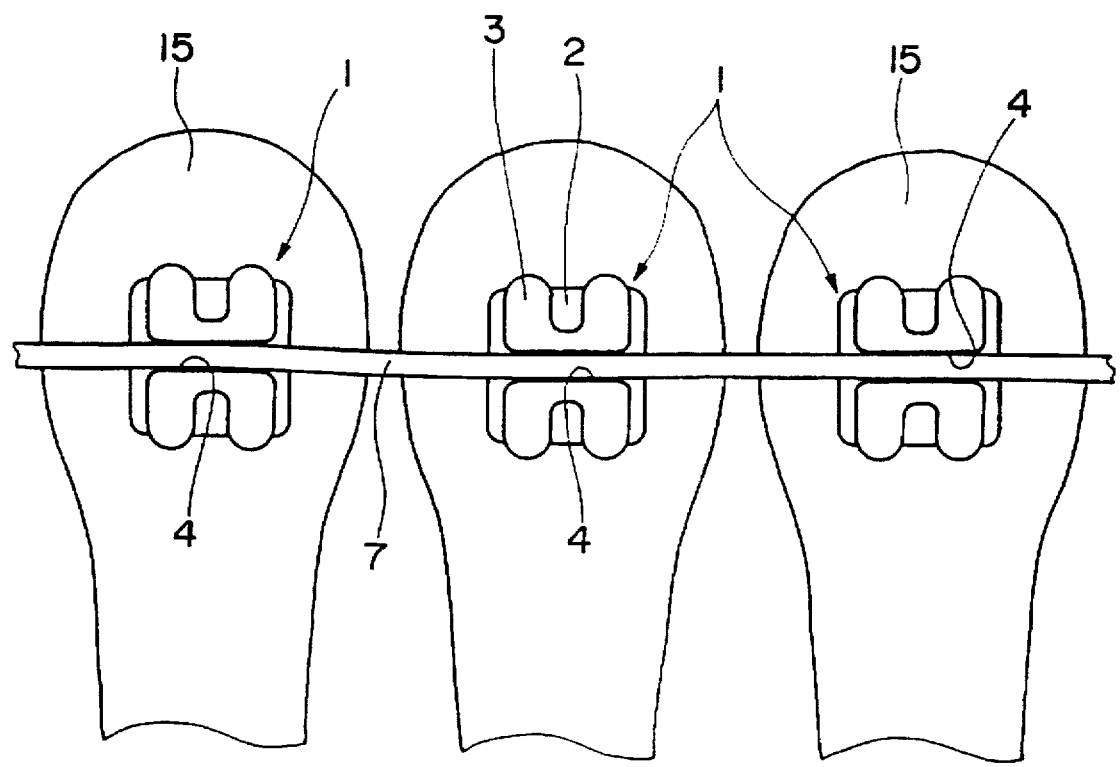
FIG. 4 is a plan view showing another embodiment.

As shown in FIG. 4, such orthodontal braces 1 are fixed to the tooth 15 by adhering the bottom plane (rear plane) 5 of base 2 to the tooth 15 by an adhesive substance. Minute indentations 6 are formed on the bottom plane 5 of base 2. See FIG. 2. In the preferred embodiment, these indentations 6 are formed as grooves, preferably in a grid formation. However, the indentations are not limited to this formation. For example, grooves formed as straight lines or as a concentric annular shape, or grooves with other types of patterns, may be formed. Alternatively, protrusions or dimples may be formed regularly or irregularly (as in scattering).

Through forming these kind of indentations 6, the surface area adhered by the adhesive is increased, and the adhesive properties (adhesive strength) for bonding of the base 2 onto tooth 15 are therefore increased. Preferably, the indentations 6 are formed so that the adhesive area increases by about 5–250%, and more preferably by about 30–100%, as compared to a case in which no indentations are formed. Further, it is preferable to set the depth of the indentations 6 at about 50–300 μm, and more preferably from about 100–150 μm.

FIG. 4 shows the state in which teeth are equipped with the dental-care device of the present invention, composed of a plurality of orthodontal braces 1 and wire 7. Each orthodontal brace 1 is adhered to the surface plane of each tooth 15 corresponding (in a fixed correspondence) through the adhesive material on the bottom plane of the base 2. Wire 7 passes through slot 4 of each orthodontal brace in a state of tension. It is through this tensile force that the load is provided to the orthodontal braces 1 for orthodontically correcting the alignment of the teeth.

Wire 7 may be composed of, for example, Ti or Ti compounds, stainless steel, or super-plastic compounds, or a combination thereof. The cross-sectional formation of the wire may be, for example, rectangular, polygonal, circular, elliptical, semi-circular, or the like.

Orthodontal braces 1, as constructed above, are composed of metal material which contains Ti as the base component, together with carbon (C) in an amount of from about 0.03–0.5 wt % by weight of the metal material, oxygen (O) in an amount of from about 0.08–0.8 wt % by weight of the metal material, and nitrogen (N) in an amount of from about 0.03–0.6 wt % by weight of the metal material.

Ti is light weight, has a high strength and a high degree of hardness; it is difficult for deformation and breakage to occur, so that it is superior in its durability and its anti-corrosive properties. Moreover, elution of the metal components is extremely small, so that allergic reactions from metal allergies and the like can be controlled, thereby providing superior compatibility with the body. Furthermore, Ti has a small metallic luster, unlike stainless steel, and it does not impair the appearance of the teeth which are being equipped with the braces.

In the metal material composing the orthodontal braces 1, C, O and N exist in a form of, for example, a chemical compound with Ti. Because these elements are well balanced in the metal material, the dental-care device maintains the physical attributes of beneficial strength, hardness, ductility (toughness), and elasticity. Among these elements, the content of N is particularly important. Even if the content amount of nitrogen is minute, a high degree of effects and improvements are seen in the physical characteristics of the metal material.

The C content in the metal material is from about 0.03–0.5 wt % by weight of the metal material, preferably from about 0.04–0.2 wt %, and even more preferably 0.05–0.1 wt %. When the C content is less than 0.03 wt %, the strength of the metal material is decreased if the amount of O and N are also small. If the C content exceeds 0.5 wt %, the ductility of the metal material is decreased.

The O content in the metal material is from about 0.08–0.8 wt % by weight of the metal material, preferably from about 0.1–0.5 wt %, and more preferably from about 0.25–0.3 wt %. If the O content is less than 0.08 wt %, and if the amounts of C and N are small, the strength of the metal material decreases. If the O content exceeds 0.8 wt %, the ductility of the metal material decreases.

The N content in the metal material is preferably from about 0.03–0.6 wt % by weight of the metal material, more preferably from about 0.35–0.14 wt %, and even more preferably from about 0.04–0.05 wt %. If the N content is less than 0.03 wt %, and if the amounts of C and O are small, the strength of the metal material decreases. If the N content exceeds 0.6 wt %, the ductility of the metal material decreases.

It is preferable that the total amount of C, O and N in the metal material is from about 0.14–1.0 wt % by weight of the metal material, more preferably from about 0.18–0.8 wt %, and even more preferably from about 0.30–0.4 wt %. If the total amount is less than 0.14 wt %, the strength of the metal material decreases. If it exceeds 1.0 wt %, the ductility of the metal material decreases.

The metal material may also contain, for example, the elements Fe, Cr, Pd, Co, Zr, Al, V, Mo, and other elements, or mixtures thereof, indispensable or intentionally, within a range not causing inflammation (reactions) from metal allergies and the like. The addition of these elements contributes additional strength to the metal material. It is preferable that these elements exist in alloy with Ti or formed with metallic compounds.

Figure 5:
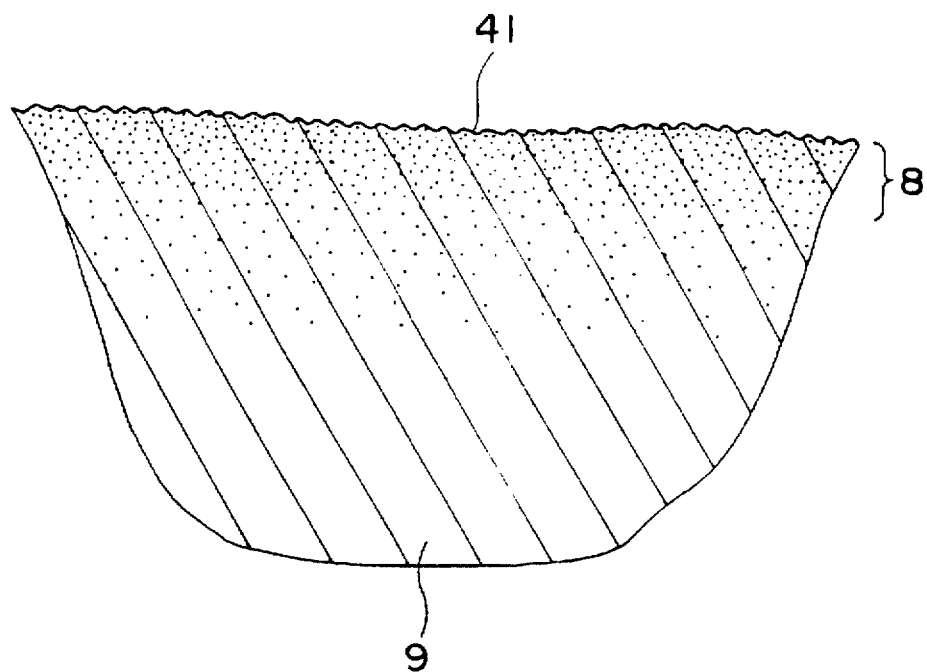
FIG. 5 is a cross sectional view denoting an enlargement of the vicinity of the inner surface of the slot in the orthodontal braces.

FIG. 5 is an enlarged cross section showing the vicinity of the inner surface 41 of slot 4 in the orthodontal braces 1. As shown in the figure, at the inner surface 41 of slot 4, the surface layer 8 is formed with a high degree of hardness as compared to the inner part 9.

There are many reasons for surface layer 8 having a high degree of hardness. However, the major reason resides in the composition of the surface layer. The total amount of C, O, and N in the surface layer 8 is large as compared to that in the inner part 9, with the average value of the total amount of C, O, and N in the surface layer 8 preferably being larger than that in the inner part 9 by about 4–60%, and more preferably about 5–20%.

As a result of the surface layer 8 having this kind of hardness, the sliding ability of wire 7 against the inner surface 41 of the slot 4 is improved (the sliding resistance is reduced), and movement of the orthodontal braces 1 against wire 7 can be easily performed, resulting in more correct and minute load adjustments.

The border between the surface layer 8 and the part on the side further in from the surface layer 8, inner part 9, does not need to be clearly defined. In the vicinity of the border, the degree of hardness may be continuously altered, or the contained elements, such as C, O, and N, may have a prescribed concentration gradient in the depth direction.

For example, in the latter case, if the total amount of C, O, and N in the surface layer 8 is defined as a% by weight of the total composition, and the total amount of C, O, and N in the part further inside from surface layer 8 (inner part 9) is defined as b% by weight, it is preferable that the thickness of the part in which the ratio a:b is equal to or greater than 1.1:1 is from about 2–100 µm, and more preferably from about 5–50 µm. If the thickness is less than 2 µm, the function of the surface layer 8, namely, the improved effect of the sliding characteristic of wire 7, will not be sufficiently demonstrated, or the durability of the effect will be inferior. If the thickness of this part exceeds 100 µm, the metal material will become brittle, breaking easily during use or at the time of removal.

The thickness of this part can be properly adjusted by controlling the burning conditions (burning temperature, burning time, vacuum of the burning atmosphere, gas composition, etc.) during the burning step in the manufacturing process of the orthodontal braces 1, which will be explained below.

The degree of hardness of surface layer 8 is not especially limited; however, it is preferable if the Vickers hardness is from about 200–400, and even more preferable if it is from about 300–380. With this range of hardness, the above-explained effects are demonstrated.

The surface layer 8 may be formed at least at the inner surface 41 of the slots 4. However, it may also be formed at other parts as well, such as covering the entire orthodontal braces 1.

Figure 6:
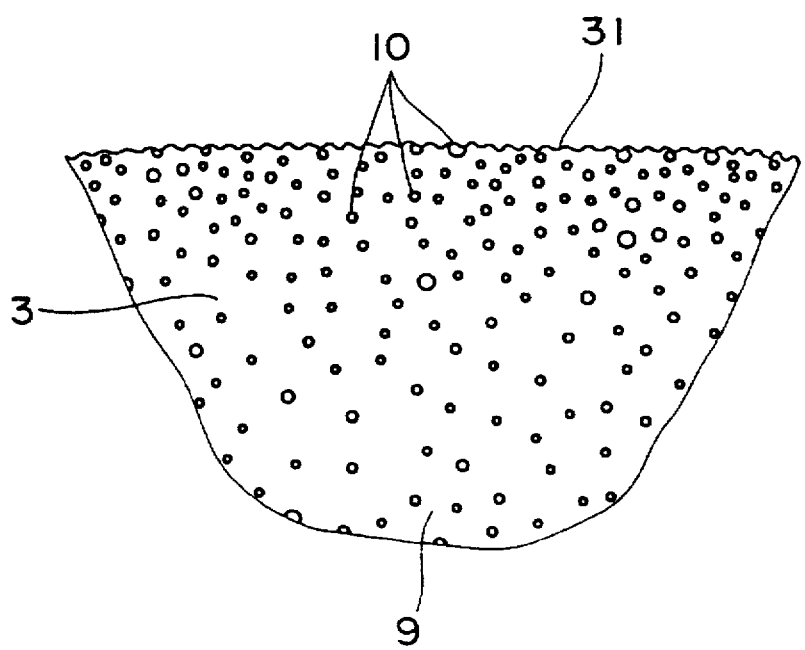
FIG. 6 is a cross-sectional figure denoting an enlargement of the vicinity of the surface of the wire receiving part in the orthodontal braces.

FIG. 6 is an enlarged cross-sectional view of the vicinity of the surface 31 of the wire receiving part 3 of the orthodontal braces 1. As shown in the figure, minute pores are scattered in the vicinity of the surface 31 of the wire receiving part 3, which contribute to the hydrophilic property (water retention function). The hydrophilic property improves the wetness characteristic of the surface 31 of the wire receiving part 3, so that when the surface 31 becomes wet with saliva, it can be maintained in a state of wetness, thus preventing dryness. Consequently, the lubricating ability to body tissue, in particular the lips and other soft tissues, including mucous membranes, can be maintained, reducing inflammatory reactions and preventing pain to the wearer of the orthodontal braces. The existence of the pores 10 also restrains the luster of the surface 31 of wire receiving part 3, which greatly improves the appearance of the braces worn on the teeth.

The average diameter of the pores is preferably from about 0.5–50 µm, and more preferably from about 5–20 µm. If the average diameter is smaller than 0.5 µm, saliva can not sufficiently penetrate, and lubricating ability is reduced. Furthermore, the appearance is impaired because of the luster.

If the average diameter exceeds 50 µm, the strength and ductility of the metal material are reduced. Further, because the open pores are large, food and the like are retained in these open pores during use, causing the propagation of bacteria and the occurrence of other deleterious effects.

It is preferable if most (in particular, more than 66%) of the pores 10 have a diameter within a range of from about 0.5–100 µm, and even more beneficial if the range is from about 5–50 µm. In this case, the function of the distribution curve is not particularly limited. For example, a Gaussian distribution (normal distribution), a binomial distribution, and the like are allowable. As a result, the wetness characteristic of surface 31 is further improved, as well as appearance.

The pores are preferably present in an amount of from about 0.05–5.0 vol % by volume of the surface 31, and even more preferably from about 0.5–2.0 vol %. If the pores are present in an amount less than 0.05 vol %, the improvement in the effect of the wetness characteristic of the surface 31 is not adequate. If the amount exceeds 5.0 vol %, the strength of the metal material, in particular tensile strength, ductility, and elasticity, is reduced.

The number of pores present may be decreased in the depth direction from the surface 31, or may be gradually decreased from the surface 31 toward the inner part 9. In the latter case, the wetness characteristic of the surface 31 can be improved while maintaining a high level of strength and ductility in the orthodontal braces 1.

The pores 10 are easily formed if the orthodontal braces 1 are manufactured through a later-explained metal powder injection molding method. The conditions relating to the pores 10 can be properly adjusted through controlling the manufacturing conditions, such as types and amount of binder, burning conditions (burning temperature, burning time, vacuum of the burning atmosphere, or the gas composition, etc.), and so on.

In the preferred embodiments, pores 10 are formed in the same way as aforesaid, in the vicinity of the bottom plane of the base 2, and particularly in the vicinity of the surface of the indentations 6. As a result, in addition to the operation of indentations 6, the maintaining characteristic of the adhesive material for fixing the orthodontal braces 1 to the teeth is further improved, and the adhering characteristic (adherence strength) for bonding of the base 2 to the teeth 15 is improved.

Although it is sufficient that the pores 10 are formed at least in the vicinity of the surface 31 of the wire receiving part 3, or in the vicinity of the bottom plane 5 of the base 2, they may be formed in other parts as well, and may even be formed throughout the entire orthodontal braces 1.

The manufacturing process of the above-explained orthodontal braces 1 is not limited to a particular technique. However, it is beneficial for the braces to be manufactured by a metal powder injection molding method (MIM: Metal Injection Molding). Below is an explanation of the metal powder injection molding method.

MIM Method

Step 1: Metal powder from Ti (or a Ti alloy) and a binding agent(s) (organic binder) are prepared and kneaded by a kneader to obtain a kneaded object (compound).

The average grain (particle) diameter of the metal powder is not limited to a particular diameter. However, a diameter of about 5–60 µm is generally preferable, and a diameter of about 10–40 µm is even more preferable.

As a binding agent, one or more of the exemplary substances from the following group may be selected: polyethylene; polypropylene; polyolefins, such as ethylene vinyl acetate copolymers; polymethyl methacrylate; polybutyl methacrylate and other acryl group resins; polystyrene and other styrene group resins; polyvinyl chloride; polyamide; polyester; polyether; thermoplastic resins, including copolymers of the above-listed substances; various types of wax; paraffin; and the like.

The binding agents are preferably added in an amount of from about 4.0–15.0 wt % by weight of the metal material, and more preferably in an amount of from about 4.0–8.0 wt %. If the added amount of the binder is less than 4.0 wt %, there will be scant fluidity during the molding, and injection molding becomes impossible or very difficult, or the composition of the molded compact becomes inhomogeneous. If the amount of the binder exceeds 15.0 wt %, the shrinkage rate increases when the molded object obtained through injection molding is burned, decreasing the accuracy of the dimensions. This may cause the number of pores or the C content to exceed the aforesaid ranges.

Moreover, various additives other than the metal powder and the binding agents may be added as necessary during kneading such as, for example, plasticizing agents, lubricating agents, antioxidants, degreasing promotion agents, and surfactants.

As an example of kneading conditions, the knead temperature may be from about room temperature to 150° C., and the knead time may be from about 60–180 minutes.

Step 2: Utilizing the kneaded object obtained from step 1, or pellets made from the kneaded object, injection molding is performed by the injection molder to form a compact having a shape of the orthodontal braces 1. The dimensions of the molded compact are set taking into account the shrinkage that will occur from the later burning step.

For the molding conditions, it is preferable if the temperature of the materials is from about 130°–170° C., and even more preferably from about 150°–160° C. It is preferable for the injection pressure to be from about 300–600 kgf/cm$^2$, and even more preferably from about 300–400 kgf/cm$^2$. It is preferred that the mold temperature be from about 5°–50° C., and even more preferably from about 10°–20° C.

Step 3: (This step may be omitted.) A binder extraction process may then be performed to the compact obtained from step 2. The binder removal is performed through heat processing under a non-oxidation atmosphere, for example, under vacuum or reduced pressure conditions, for example, $1 \times 10^{-1}$ to $1 \times 10^{-6}$ Torr.

In this case, it is preferable for the heat processing conditions to be at a temperature from about 50°–650° C., for about 8–72 hours, and even more preferably at about 60°–550° C., for about 12–18 hours.

The binder extraction process (degreasing process) may be performed by elution of specific components of the binder(s), utilizing a predetermined solvent of fluid or gas.

Step 4: Next, the compact obtained from either Step 2 or Step 3 is burned to produce a metallic sinter. The burning may be performed once or multiple times.

It is preferable that the burn conditions are at a temperature of from about 400°–1400° C., for about 10–26 hours, and more preferable that the temperature be from about 500°1350 C., for about 15–18 hours. In this case, the burn atmosphere is a non-oxidation atmosphere, proceeding, for example, in argon gas or other inactive gases, under a vacuum or reduced pressure conditions, for example, from about $1 \times 10^{-2}$ to about $1 \times 10^{-6}$ Torr, or in other atmospheres with reducing properties.

When the surface layer 8 is formed, gas(es) containing at least one of C, O or N is/are injected into the burning atmosphere in the middle of the burning step. For example, appropriate gases may be selected from air, $O_2$ gas, $CO_2$ gas, CO gas, $N_2$ gas, methane gas, acetylene gas, propane gas and mixtures thereof and the like. By controlling the burning conditions, such as the composition of the injected gas, the gas injection amount (partial pressure of the gases in the burning atmosphere), and the post-injection burning time, the conditions of the surface layer 8 described above are determined.

Step 5: As necessary, surface treatment is performed to the surface of the obtained metal sintered compact. For example, shot blasting, honing, grinding, etching, wet plating, vacuum evaporation, ion plating, spattering, CVD, thermal spraying, and other surface processing may be performed. If the surface layer 8 is formed only with necessary parts (for example, the inner surface 41 of the slots 4), unnecessary parts of the surface layer 8 can be removed by grind processing, etching, and the like.

The orthodontal braces 1 formed from the metal sintered compact are obtained by going through the steps explained above.

The metal powder injection molding method described above can eliminate problems seen in the conventional casting method, such as casting defects or liquid flow. Moreover, even a delicate dental device with a complicated shape can be formed monolithically, achieving easy manufacturing with good repeatability. In particular, conventional methods require performing grind processing or fixing meshed material onto the bottom plane 5 of the base 2. However, in the present invention, minute indentations 6 or slot 4 can be monolithically and simultaneously formed without performing these types of operations. This improves the accuracy of the dimensions and yield rate, in addition to facilitating manufacturing.

Through adjustment of types of binding agents, added amounts, binder extraction conditions, and burning conditions, the desired conditions for the composition of the metal materials composing the braces for orthodontal correction, in particular the composition of the surface layer, the pore diameter, or the number of pores, can be set, which is an advantage.

Moreover, with the metal powder injection molding method, minute indentations can be formed on the surface of the metal material, in particular on the inner surface 41 of slot 4, or on the bottom plane 5 of the base 2, as the sintered surface. See FIGS. 10–12. As a result, the sliding characteristic of the wire 7 or adhesion to the teeth, respectively, is further improved.

These minute indentations also contribute to an improved wetness characteristic of the surface, as previously explained. The characteristics of the minute indentations can be controlled by setting the selection of the Ti powder, molding conditions, or sintering conditions.

Although in the preferred embodiments the orthodontal braces 1 are obtained by monolithically forming the base 2 and the wire receiving part 3 through a metal powder injection molding method, the base 2 and the wire receiving part 3 may be manufactured separately and adhered together. In this case, the base 2 and the wire receiving part 3 may each be respectively manufactured by the metal powder injection molding method or by other methods.

EXAMPLES

Presented below are examples of embodiments of the dental-care device of the present invention. The weight percent is of the total metal material unless otherwise indicated.

Example 1

Orthodontal braces are manufactured in the form shown in FIGS. 1–3, as explained below, using the metal powder injection molding method.

First, Ti powder having an average grain diameter of 20 μm was mixed with 2.6 wt % of ethyleneglycidyl methacrylate-vinyl acetate copolymer, 1.6 wt % of dibutyl phthalate, 2.8 wt % of wax, and 3.0 wt % of styrene, which are added as binders or for some other function. The mixture was kneaded at 130° C. for 60 minutes in air to obtain a kneaded object (compound).

Figure 1:
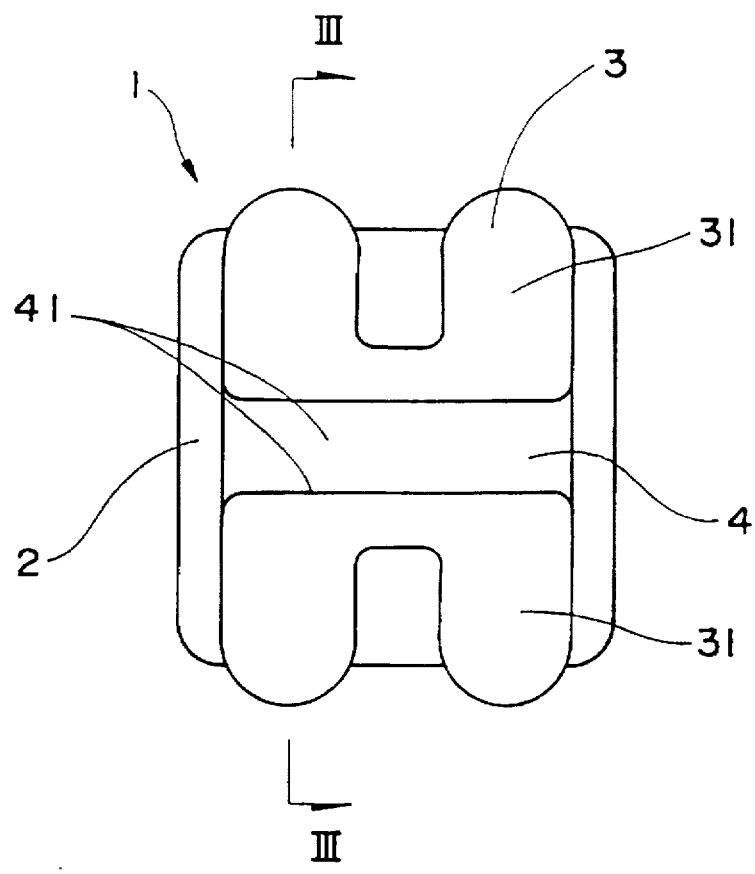
FIG. 1 is a plan view of an embodiment of the dental care device of the invention, applied to orthodontal braces.
Figure 2:
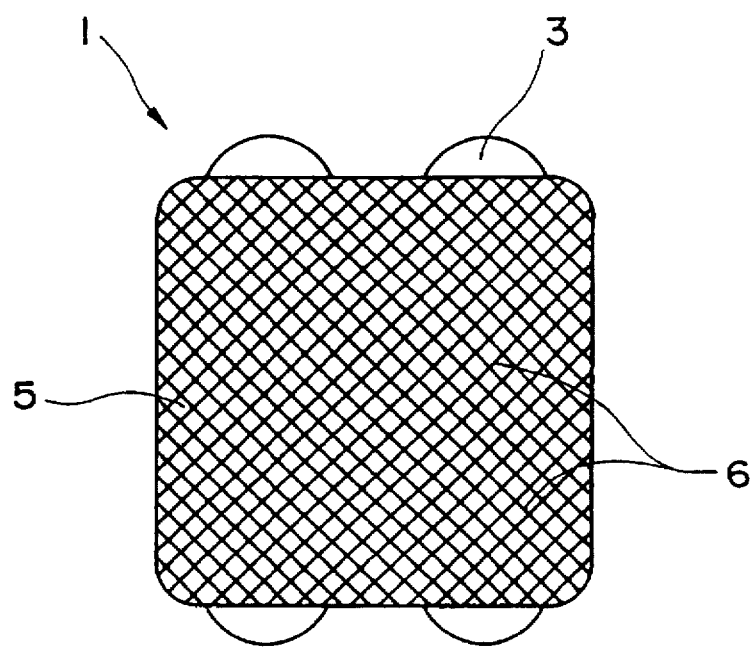
FIG. 2 is a bottom view of the embodiment of FIG. 1.

Using this kneaded object, a compact of the orthodontal braces 1, in the formation shown in FIGS. 1–3, was manufactured by injection molding using an injection molder. The mold conditions at this time are 150° C. for the material temperature, 400 kgf/cm$^2$ for the injection pressure, and 20° C. for the metal mold temperature.

Next, as a binder extraction process on the obtained compact, the temperature was raised from 60° C. to 450° C. over 17 hours under the reduced pressure of $1 \times 10^{-2}$ Torr, and then was maintained at 450° C. for one hour and was cooled to the normal temperature.

The compact resulting from the binder extraction process was heated from 600° C. to 1300° C. for 15 hours in a vacuum (5×10⁻⁶ Torr), and was burned at 1300° C. for 3 hours to obtain orthodontal braces composed from a metal sintered compact containing Ti as the major component.

The specifications for the various parts of the orthodontal braces are as follows:

| | |
|---|---|
| Dimensions of base: | 5 mm × 5 mm |
| Form of the indentations: | grid formed channels (both vertical and horizontal at 0.5 mm intervals) |
| Depth of the indented part of the indentations: | 120 μm |
| Increase in adhesive surface area by indentations: | 62% |
| Depth of slot: | 2.5 mm |
| Width of slot: | 1.3 mm |

Example 2

Orthodontal braces were manufactured as in Example 1, except that the amount of dibutyl phthalate was increased by 1.4 wt%, and the amount of Ti metal powder was reduced by that amount.

Example 3

Orthodontal braces were manufactured as in Example 1, except that kneading of the mixture containing Ti metal powder was performed in an atmosphere rich with nitrogen gas (nitrogen gas amount 95%, with the remainder oxygen).

Example 4

Orthodontal braces were manufactured as in Example 1, except that during the binder extraction process the compound was heated with the final temperature being 550° C. for 60 minutes under a reduced pressure of $1 \times 10^{-1}$ Torr.

Example 5

Orthodontal braces were manufactured as in Example 1, except that the final burning temperature in the burning step of the compact formed after the binder extraction was 1200° C., maintained for 2.5 hours.

Example 6

Orthodontal braces were manufactured as in Example 1, except that the pressure of the burning atmosphere was set to a vacuum state ($1 \times 10^{-4}$ Torr) in the burning step of the compact after it was subjected to the binder extraction.

Example 7

Orthodontal braces were manufactured as in Example 1, except that in place of Ti metal powder, a compound metal powder with an average grain diameter of 20 μm was formed of Ti, Al of 6 wt %, and V of 4 wt %. The burn atmosphere was argon of a high purity, with a vacuum of $5 \times 10^{-2}$ Torr.

Example 8

Orthodontal braces were manufactured as in Example 1, except that the metal mold in the injection molding was changed so that a number of dimples of 600 μm diameter and a depth of 150 μm were formed, scattered on the bottom plane of the base.

The increase of the adhesive surface area due to the formation of the indentations was 90%.

Example 9

Orthodontal braces were manufactured as in Example 1, except that the burning of the compact was performed as described below, and the surface layer was formed on the entire orthodontal brace.

In the burn process, the compact was burned at 1300° C. for two hours in a vacuum ($2 \times 10^{-6}$ Torr). Then nitrogen gas was injected into the burn atmosphere and burning continued for 1 hour at 1300° C. in the burn atmosphere with the vacuum at $3 \times 10^{-4}$ Torr.

Example 10

Orthodontal braces were manufactured as in Example 1, except that the burning of the compact was performed as described below, and the surface layer was formed on the entire orthodontal brace.

In the burn process, the compact was burned at 1300° C. for 1.5 hours in a vacuum ($2 \times 10^{-6}$ Torr). Then, nitrogen gas and methane gas were injected into the burn atmosphere in the same amount and burning continued for 1.5 hours at 1300° C. in the burn atmosphere with the vacuum at $3 \times 10^{-4}$ Torr.

Example 11

Orthodontal braces were manufactured as in Example 1, except that the burning of the compact was performed as described below, and the surface layer was formed on the entire orthodontal brace.

In the burn process, the compact was burned at 1300° C. for 2 hours in a vacuum ($5 \times 10^{-6}$ Torr). Then, nitrogen oxide gas, acetylene gas, and methane gas were injected into the burn atmosphere in the same amount and burning continued for 1 hour at 1300° C. in the burn atmosphere with a vacuum at $3 \times 10^{-4}$ Torr.

Comparison Example 1

Orthodontal braces were manufactured as in Example 1, except that the binder extraction process was omitted, the atmosphere in the compact burn process was a nitrogen gas atmosphere with a vacuum degree of $5 \times 10^{-3}$ Torr, and the burn temperature and burn time were set to 1100° C. and 2 hours, respectively.

Comparison Example 2

JIS-1 type pure Ti plate (completely annealed material) was used as the source material, and cutting, grinding, polishing and the like were performed to the Ti plate to obtain orthodontal braces with substantially the same shape as in Example 1.

A number of dimples were formed as scattered dots on the bottom plane of the base in the orthodontal braces, with a diameter of 600 μm, and a depth of 150 μm.

Comparison Example 3

Completely annealed material of stainless steel (SUS316L) was used as the source material. Cutting, grinding, and polishing were performed to obtain orthodontal braces similar to those in Comparison Example 1.

COMPOSITION OF METAL MATERIALS

The composition of the metal materials, specifically the content amount of C, O, and N in Examples 1–11 and Comparison Examples 1–3, was analyzed using EC-12, RO-116, and TN-114 manufactured by LECO. The results are shown in Table 1.

Figure 7:
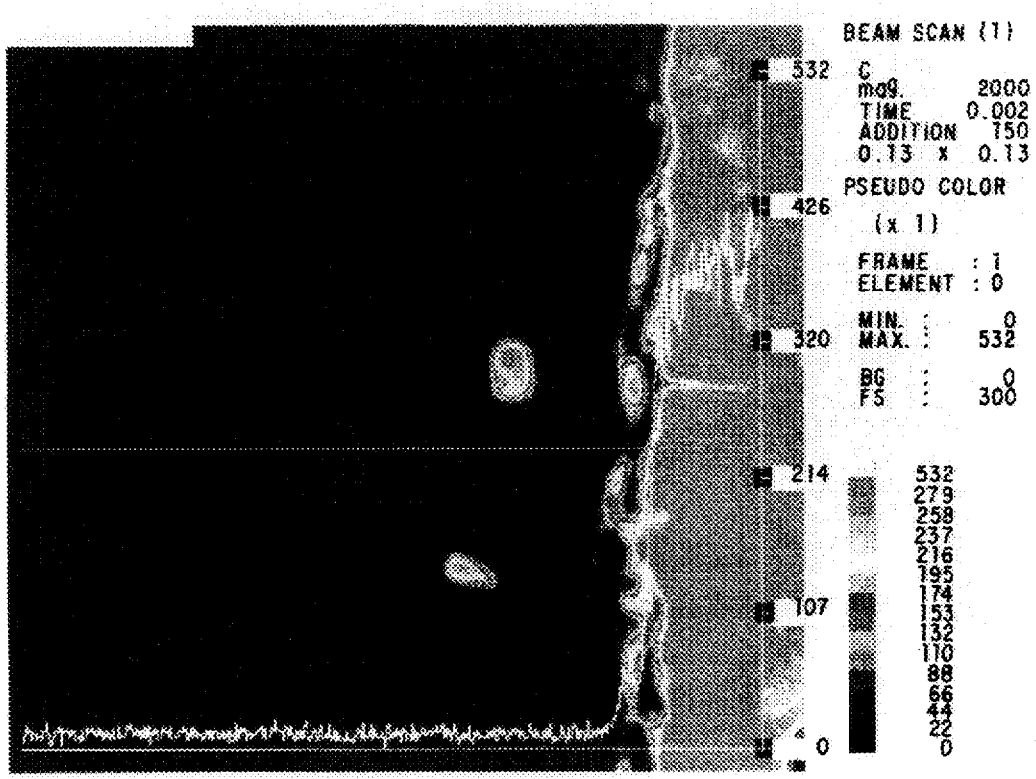
FIG. 7 is a graph denoting the results of the line analysis of carbon (C), according to an electronic line microanalyzer, in the cross-sectional part denoting an enlargement of the vicinity of the surface of the wire receiving part in the orthodontal braces.
Figure 8:
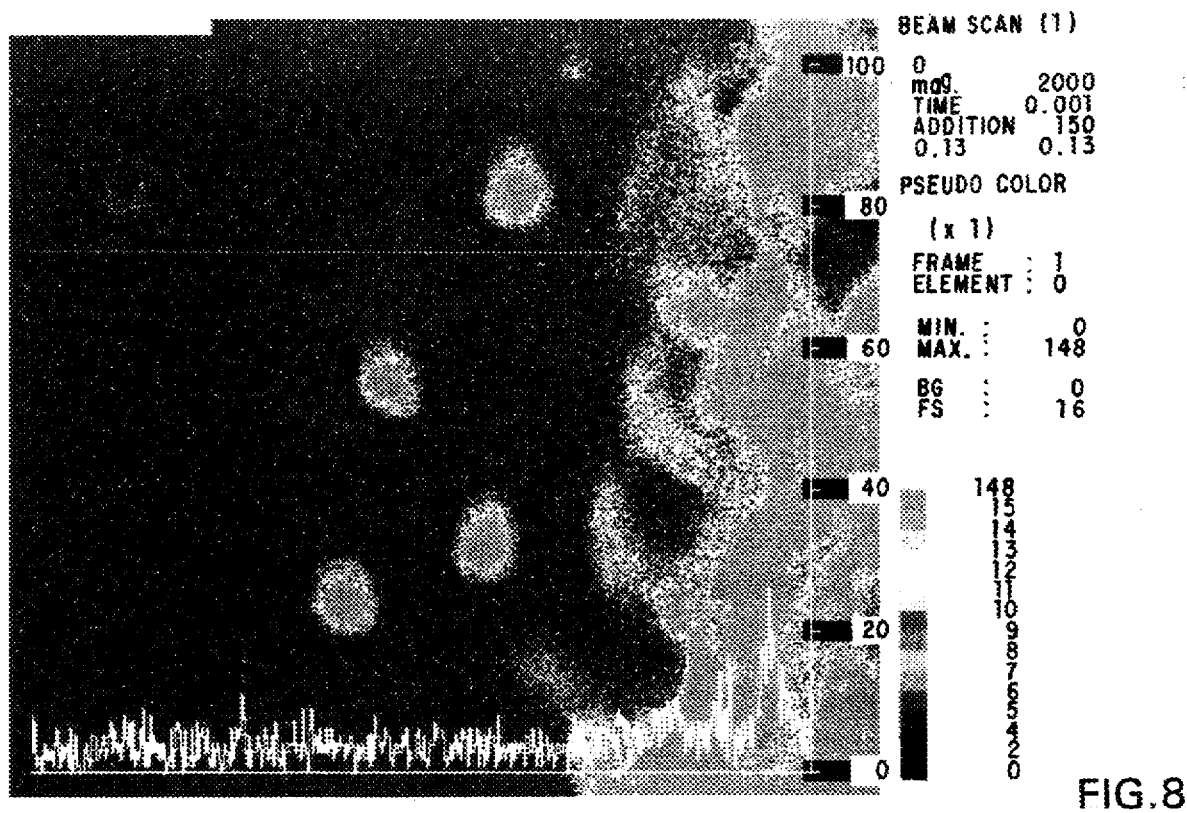
FIG. 8 is a graph denoting the results of the line analysis of oxygen (O), according to an electronic line microanalyzer, in the cross-sectional part denoting an enlargement of the vicinity of the surface of the wire receiving part in the orthodontal braces.
Figure 9:
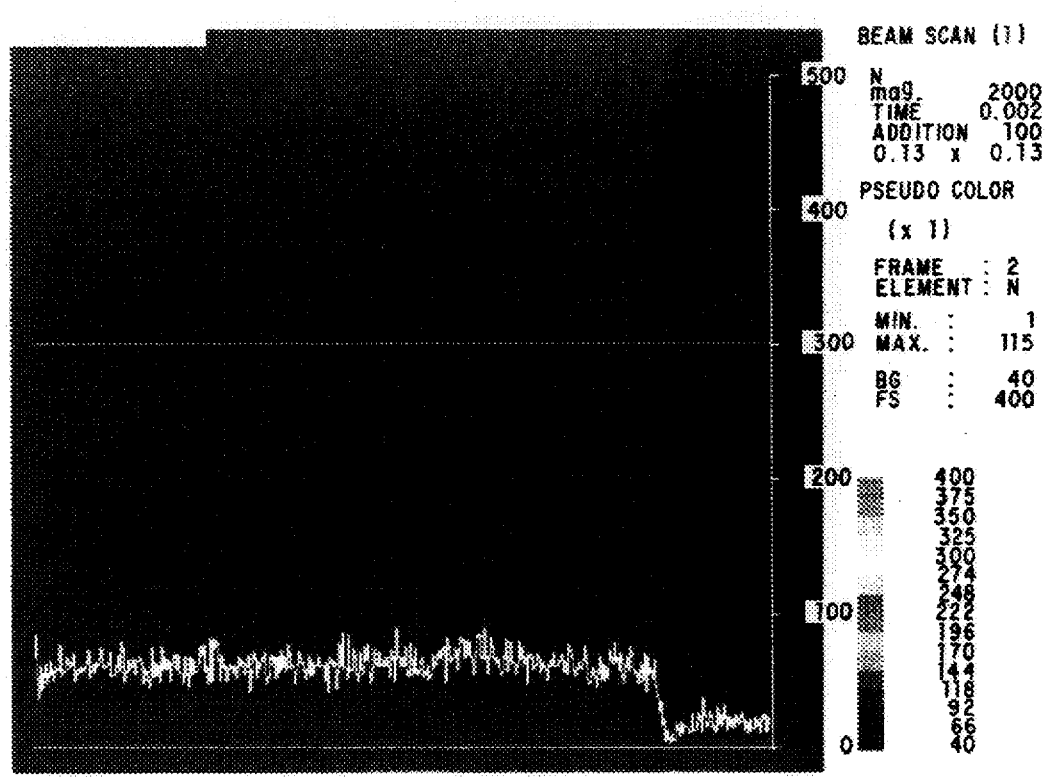
FIG. 9 is a graph showing the results of the line analysis of nitrogen (N), according to an electronic line microanalyzer, in the cross-sectional part denoting an enlargement of the vicinity of the surface of the wire receiving part in the orthodontal braces.

In the data analysis of Example 4, line analysis of C, O, and N was performed by an electronic line microanalyzer (EPMA-8705 manufactured by Shimazu Manufacturing Co., Ltd.), and the results are shown in FIGS. 7, 8, and 9.

Regarding Examples 9, 10, and 11, when the total content amount of C, O, and N in the surface layer is defined as "a", and the total content amount of C, O, and N in the center part is defined as "b", the thicknesses of the parts in which a:b ≧1.1:1, are, respectively, 28 μm, 40 μm, and 33 μm.

TABLE 1

|  | Inner Part (wt. %) | | | | Surface Layer (wt. %) | | | | Amount of C, O and N in the Entire Brace (wt. %) |
| --- | --- | --- | --- | --- | --- | --- | --- | --- | --- |
|  | % C | % O | % N | % Total | % C | % O | % N | % Total |  |
| Example 1 | 0.04 | 0.08 | 0.04 | 0.16 | — | | | | — |
| Example 2 | 0.05 | 0.10 | 0.03 | 0.18 | — | | | | — |
| Example 3 | 0.08 | 0.10 | 0.13 | 0.31 | — | | | | — |
| Example 4 | 0.48 | 0.08 | 0.03 | 0.59 | — | | | | — |
| Example 5 | 0.07 | 0.11 | 0.05 | 0.23 | — | | | | — |
| Example 6 | 0.04 | 0.78 | 0.09 | 0.91 | — | | | | — |
| Example 7 | 0.06 | 0.08 | 0.04 | 0.18 | — | | | | — |
| Example 8 | 0.06 | 0.09 | 0.05 | 0.20 | — | | | | — |
| Example 9 | 0.06 | 0.14 | 0.58 | 0.78 | 0.07 | 0.15 | 0.63 | 0.85 | 0.79 |
| Example 10 | 0.28 | 0.13 | 0.48 | 0.89 | 0.43 | 0.22 | 0.77 | 1.42 | 0.97 |
| Example 11 | 0.22 | 0.24 | 0.40 | 0.86 | 0.32 | 0.38 | 0.60 | 1.30 | 0.93 |
| Comparative Example 1 | 0.06 | 0.82 | 0.89 | 1.77 | — | | | | — |
| Comparative Example 2 | 0.01 | 0.07 | 0.01 | 0.09 | — | | | | — |
| Comparative Example 3 | 0.02 | 0.005 | — | 0.025 | — | | | | — |

CONDITIONS RELATING TO PORES

Figure 10:
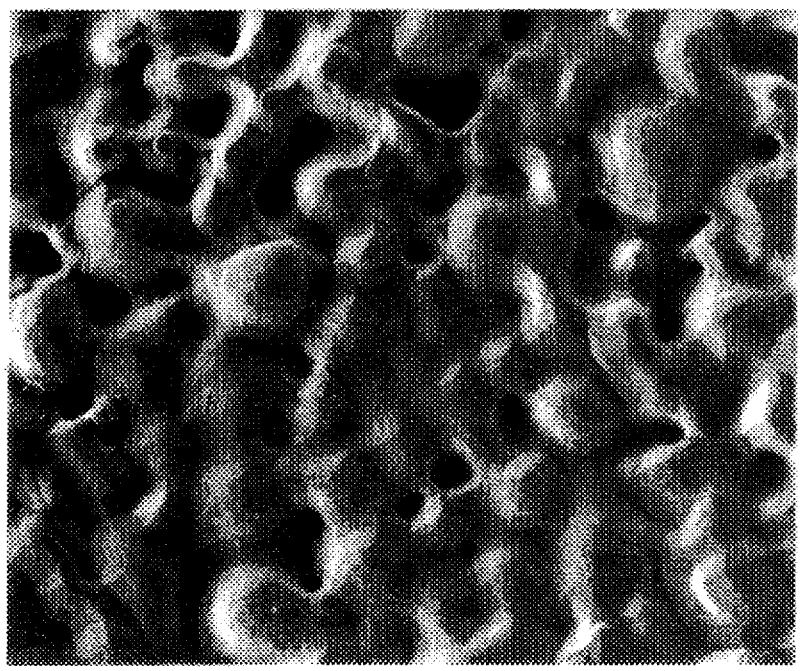
FIG. 10 is a photograph showing the metal composition.
Figure 11:
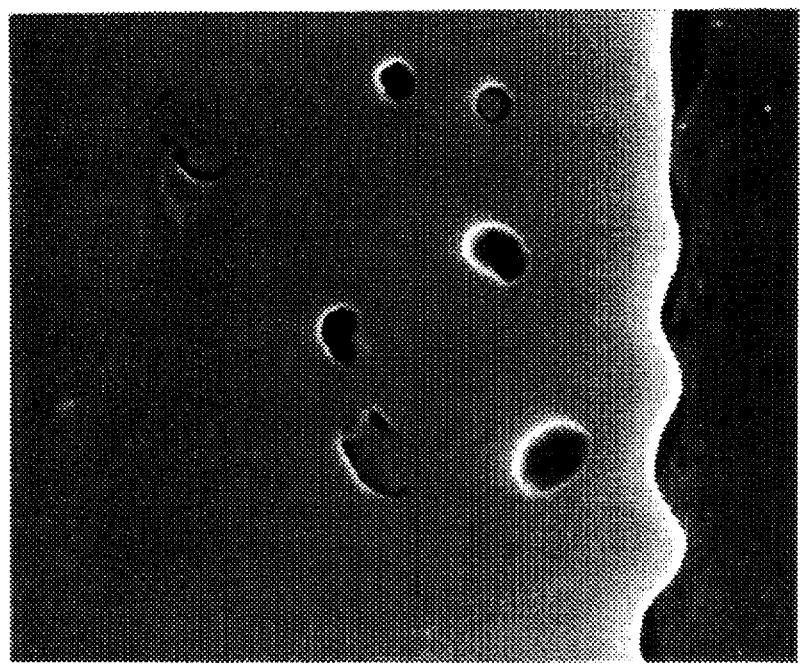
FIG. 11 is a photograph showing the metal composition.
Figure 12:
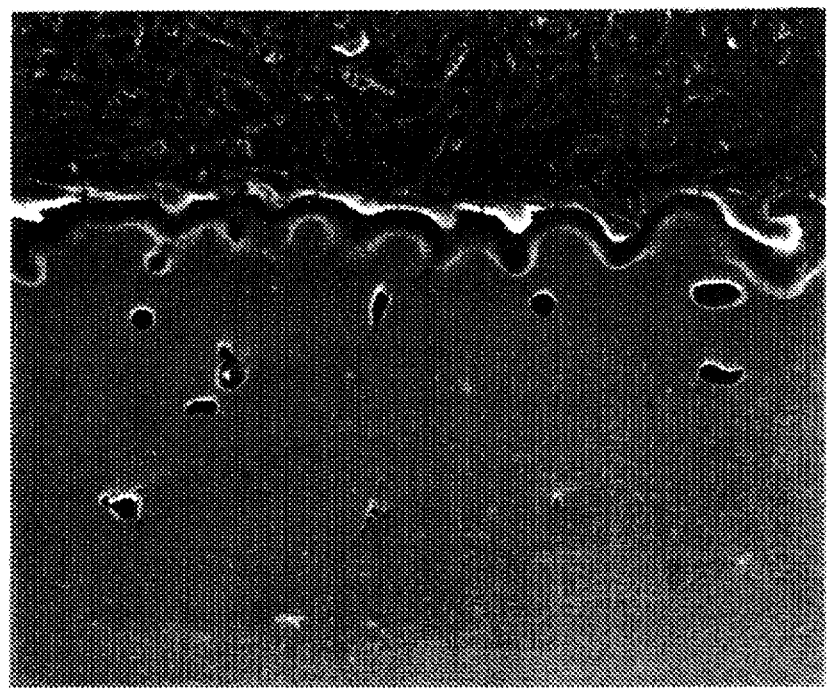
FIG. 12 is a photograph showing the metal composition.

With regard to the orthodontal braces in Examples 1–11, and Comparison Examples 1–3, electronic microscopic pictures were taken of the surface of the wire receiving part and of a cross section of the vicinity of the surface of the wire receiving part. An electronic microscopic picture of the surface of the wire receiving part in Example 4 (magnified 500 times) and an electronic microscopic picture of the cross sectional surface in the vicinity of the surface of the wire receiving part (magnified 1000 times) are shown in FIG. 10 and FIG. 11, respectively. An electronic microscopic picture of a cross sectional surface in the vicinity of the surface of the wire receiving part in Example 9 (magnified 400 times) is shown in FIG. 12.

In addition, with reference to each of the electronic microscopic pictures, the pore diameters, the distribution of the pores, and the average diameter of the pores were determined. Also, the number of pores was determined from a density ratio. The results of those calculations are shown in the following Table 2.

TABLE 2

|  | Distribution of Pore Diameters* (%) | | | | | Average Pore Diameter (μm) | Amount of Pores (%) |
| --- | --- | --- | --- | --- | --- | --- | --- |
|  | 1 | 2 | 3 | 4 | 5 | | |
| Example 1 | 34 | 52 | 11 | 3 | 0 | 12.3 | 0.06 |
| Example 2 | 35 | 54 | 9 | 1 | 1 | 13.1 | 0.08 |
| Example 3 | 3 | 28 | 51 | 16 | 2 | 23.2 | 2.43 |
| Example 4 | 28 | 49 | 19 | 3 | 1 | 17.2 | 2.10 |
| Example 5 | 1 | 7 | 16 | 24 | 52 | 48.7 | 4.82 |
| Example 6 | 1 | 3 | 8 | 58 | 30 | 43.6 | 4.43 |
| Example 7 | 36 | 53 | 10 | 1 | 0 | 12.8 | 0.07 |
| Example 8 | 26 | 56 | 12 | 4 | 1 | 13.4 | 0.10 |
| Example 9 | 4 | 23 | 58 | 12 | 3 | 28.3 | 4.03 |
| Example 10 | 1 | 2 | 12 | 53 | 32 | 38.5 | 4.24 |
| Example 11 | 1 | 4 | 18 | 49 | 28 | 33.4 | 4.12 |
| Comparison Example 1 | 1 | 3 | 8 | 15 | 73 | 78.4 | 6.23 |
| Comparison Example 2 | — | — | — | — | — | — | — |

TABLE 2-continued

|  | Distribution of Pore Diameters* (%) | | | | | Average Pore Diameter (μm) | Amount of Pores (%) |
| --- | --- | --- | --- | --- | --- | --- | --- |
|  | 1 | 2 | 3 | 4 | 5 | | |
| Comparison Example 3 | — | — | — | — | — | — | — |

*1: 0.5 μm ≦ diameter < 10 μm
2: 10 μm ≦ diameter < 20 μm
3: 20 μm ≦ diameter < 30 μm
4: 30 μm ≦ diameter < 40 μm
5: 40 μm ≦ diameter < 50 μm

EXPERIMENTAL DATA

The orthodontal braces in Examples 1–11 and Comparison Examples 1–3 were evaluated for the items 1–8 below. The results are shown in Table 3.

1. Mechanical Strength (resistance to bending force)

The resistance to bending force was measured with a test piece after sintering, based on JIS Z 2203.

2. Adhesive Strength 0.1 g of 4-META, MMA type adhesive was applied to the bottom plane of the base of the orthodontal braces and allowed to adhere and harden onto artificial teeth. The braces and artificial teeth were then fixed by a wire. The adhesive strength was then measured using a tensile tester.

3. Hardness

Based on JIS Z 2244, the Vickers hardness HV of the inner surface of the slot was measured (load weight 5 g).

4. Sliding Resistance of the Wire

Stainless steel wire, having a square cross section of 0.014×0.014 inch$^2$ was prepared, and inserted through the slots of the orthodontal braces. An end of the wire was fixed, and sufficient tension was given to the other end by pulling it to measure the sliding resistance of the wire against the inner surface of the slot. The measured sliding resistance for each Example and Comparison Example was compared and relatively evaluated.

5. Elution Amount of the Metal Component

After soaking the orthodontal braces in a 0.05% hydrochloric solution for three months, the concentration of metal ions in the solution was quantitatively analyzed by a plasma illumination analyzing device.

The smaller the amount of the elution, the more compatible it is to body tissue.

6. Surface Wetness

After soaking one hundred of the orthodontal braces of identical shape for 10 minutes in water to which ultrasonic waves (100,000 Hz) were applied, the orthodontal braces were left in an atmosphere with a temperature of 60° C. and a humidity of 50%RH to measure the time for the surface of the wire receiving part (surface of the tie wing) to dry. The longer the time, the better the wetness characteristic.

7. Appearance (Shininess)

The degree of shininess (metal luster) of the surface metal was judged by eye. Four levels of evaluations were made: a square, a circle, a triangle, and a cross (in order, beginning from a small amount of metal luster indicating a better appearance).

8. Ease of Removal of the Braces 0.1 g of 4-META, MMA type adhesive was applied to the bottom surface of the base of the orthodontal braces and allowed to adhere and harden onto the test teeth. The braces were then left soaking in physiological saline solution at 37° C. for 200 days.

Next, the test tooth wearing the brace was held. The brace was pinched by medical forceps and twisted, being careful not to damage the brace, to remove it from the tooth. At this time, the degree of twisting force, the number of times that twisting force was applied, and controllability were comprehensively determined and evaluated in four levels, namely, a square, a circle, a triangle, and a cross, as to the ease in removing the braces.

surface layers with a high degree of hardness, are excellent as to the sliding characteristic of the wire and anti-friction.

In the orthodontal braces of Comparison Example 1, the concentration of C, O, and N in the metal material is too high and, therefore, the mechanical strength is weak, making the removal of the braces difficult. In the orthodontal braces of Comparison Example 2, because the metal mixture is dense, and because there are almost no pores, the adhesive strength is low and the surface wetness is unfavorable.

Because the orthodontal braces of Comparison Example 3 also have almost no pores, the adhesive strength is low and the surface wetness is unfavorable, as in Comparison Example 2. In addition, the compatibility with the body tissue is unfavorable due to the elution of Ni and Cr. Further, the amount of reflection of light (shininess) of the metal is large, so that the quality of the appearance is low. The orthodontal braces of Comparison Examples 1-3 also have unsatisfactory sliding characteristics of the wire.

The dental-care device of the present invention was described above based on the structures shown in the Figures. However, the present invention is not limited to the scope of the description. For instance, the form (shape) of the orthodontal braces is not limited to the form shown in the figures. Also, the wire receiving part can have a plurality of tie-wings.

In addition, the dental-care device of the present invention is not limited to a use related to the orthodontal braces described above. It can be applied to a prosthodontial attachment, artificial roots of teeth and parts thereof, and other various kinds of dental or oral surgery medical tools.

What is claimed is:

1. A dental-care device comprising orthodontal braces comprising a planar base and a wire receiving part positioned on a top surface of the base and having a slot through

TABLE 3

| | Resistance to Bending Force (Kg/mm$^2$) | Adhesive Strength (g/mm$^2$) | Vickers Hardness (HV) | Sliding Resistance of the Wire* | Metal Component Elution Amount (ppm) | Surface Wetness (sec.) | Appearance | Ease of Removal |
|---|---|---|---|---|---|---|---|---|
| Example 1 | 69 | 512 | 230 | 77 | <0.1 | 380 | ○ | ○ |
| Example 2 | 67 | 498 | 250 | 76 | <0.1 | 391 | ○ | ○ |
| Example 3 | 84 | 552 | 318 | 78 | <0.1 | 402 | □ | ○ |
| Example 4 | 78 | 550 | 323 | 79 | <0.1 | 388 | □ | ○ |
| Example 5 | 99 | 588 | 288 | 77 | <0.1 | 512 | □ | ○ |
| Example 6 | 97 | 579 | 348 | 51 | <0.1 | 488 | □ | ○ |
| Example 7 | 72 | 504 | 244 | 78 | <0.1 | 399 | ○ | □ |
| Example 8 | 65 | 824 | 277 | 78 | <0.1 | 393 | ○ | □ |
| Example 9 | 89 | 562 | 353 | 62 | <0.1 | 455 | □ | ○ |
| Example 10 | 94 | 578 | 372 | 54 | <0.1 | 480 | □ | ○ |
| Example 11 | 91 | 568 | 362 | 58 | <0.1 | 461 | □ | ○ |
| Comparative Example 1 | 58 | — | 586 | 106 | <0.1 | 540 | □ | △-x |
| Comparative Example 2 | — | 436 | 182 | 100 | <0.1 | 298 | △ | □ |
| Comparative Example 3 | — | 428 | 164 | 116 | 20.90 | 266 | x | □ |

*Sliding resistance is measured by relative ease, with Comparative Example 2 having a sliding resistance of 100.

As shown in Table 3, all of the orthodontal braces described in Examples 1 through 11 are high in mechanical strength (resistance to bending force) and adhesive strength. In addition, they are high in surface hardness, and are excellent as to the sliding characteristic of the wire, anti-friction, compatibility with body tissue, surface wetness, and ease of removal. Moreover, since they have less metal luster, they give an excellent appearance. In particular, the orthodontal braces in Examples 9 through 11, which have which a wire is passed, wherein the orthodontal braces comprise a metal material comprising a Ti base component, 0.03–0.5 wt % by weight of the metal material of carbon (C), 0.08–0.8 wt % by weight of the metal material of oxygen (O), and 0.03–0.6 wt % by weight of the metal material of nitrogen (N), and wherein a surface layer at an inner surface of the slot has a higher degree of hardness than an inner part of the wire receiving part.

2. The dental-care device of claim 1, in which a bottom surface of the planar base comprises minute indentations.

3. The dental-care device of claim 1, wherein a surface layer at an inner surface of the slot comprises a larger total amount of C, O and N than at an inner part of the wire receiving part.

4. The dental-care device of claim 3, wherein the total amount of C, O and N in the surface layer comprises a% by weight of the metal material, and the total amount of C, O and N at the inner part comprises b% by weight of the metal material, the surface layer is 2–100 μm thick, and the ratio a:b is equal to or greater than 1.1:1.

5. The dental-care device of claim 1, wherein a surface layer of the wire receiving part is hydrophilic.

6. The dental-care device of claim 1, wherein a surface layer of the wire receiving part comprises scattered pores of an average diameter of 0.5–50 μm.

7. The dental-care device of claim 6, wherein the diameters of the pores are in a range of 0.5–100 μm.

8. The dental-care device of claim 6, wherein the number of pores is 0.05–5.0% by volume of the surface layer.

9. The dental-care device of claim 8, wherein the number of pores gradually decreases from the surface layer toward an inner part of the wire receiving part.

10. The dental-care device of claim 1, wherein a bottom surface layer of the base comprises scattered pores of an average diameter of 0.5–5.0 μm.

11. The dental-care device of claim 10, wherein the diameters of the pores are in a range of 0.5–100 μm.

12. The dental-care device of claim 10, wherein the number of pores is 0.05–5.0% by volume of the bottom surface layer.

13. The dental-care device of claim 12, wherein the number of pores gradually decreases from the bottom surface layer toward an inner part of the base.

14. A dental-care device according to claim 11, comprising a plurality of said planar bases and wire receiving parts, wherein said wire is passed through the slot in each said wire receiving part.

15. The dental-care device of claim 1, wherein said orthodontal braces are manufactured by a metal powder injection molding method.

16. A dental-care device comprising orthodontal braces comprising a planar base and a wire receiving part positioned on a top surface of the base and having a slot through which a wire is passed, wherein the orthodontal braces comprise a metal material comprising a Ti base component, 0.03–0.5 wt % by weight of the metal material of carbon (C), 0.08–0.8 wt % by weight of the metal material of oxygen (O), and 0.03–0.6 wt % by weight of the metal material of nitrogen (N), and wherein a surface layer at an inner surface of the slot comprises a larger total amount of C, O and N than at an inner part of the wire receiving part.

17. The dental-care device of claim 16, in which a bottom surface of the planar base comprises minute indentations.

18. The dental-care device of claim 16, wherein the total amount of C, O and N in the surface layer comprises a% by weight of the metal material, and the total amount of C, O and N at the inner part comprises b% by weight of the metal material, the surface layer is 2–100 mm thick, and the ratio a:b is equal to or greater than 1.1:1.

19. The dental-care device of claim 16, wherein a surface layer of the wire receiving part is hydrophilic.

20. The dental-care device of claim 16, wherein a surface layer of the wire receiving part comprises scattered pores of an average diameter of 0.5–50 mm.

21. The dental-care device of claim 16, wherein a bottom surface layer of the base comprises scattered pores of an average diameter of 0.5–5.0 mm.

22. A dental-care device comprising orthodontal braces comprising a planar base and a wire receiving part positioned on a top surface of the base and having a slot through which a wire is passed, wherein the orthodontal braces comprise a metal material comprising a Ti base component, 0.03–0.5 wt % by weight of the metal material of carbon (C), 0.08–0.8 wt % by weight of the metal material of oxygen (O), and 0.03–0.6 wt % by weight of the metal material of nitrogen (N), and wherein a surface layer of the wire receiving part comprises scattered pores of an average diameter of 0.5–50 mm.

23. The dental-care device of claim 22, in which a bottom surface of the planar base comprises minute indentations.

24. The dental-care device of claim 22, wherein the diameters of the pores are in a range of 0.5–100 mm.

25. The dental-care device of claim 22, wherein the number of pores is 0.05–5.0% by volume of the surface layer.

26. The dental-care device of claim 25, wherein the number of pores gradually decreases from the surface layer toward an inner part of the wire receiving part.

* * * * *